United States Patent [19]
Guerrant

[11] Patent Number: 5,413,119
[45] Date of Patent: May 9, 1995

[54] PROTECTIVE EYE SHIELD FOR DENTAL PATIENTS

[76] Inventor: George H. Guerrant, 2901-A Loring Dr., Loring AFB, Me. 04751

[21] Appl. No.: 197,757
[22] Filed: Feb. 17, 1994
[51] Int. Cl.⁶ .............................................. A61F 9/00
[52] U.S. Cl. ..................................... 128/858; 128/857; 2/452; 2/447
[58] Field of Search ............... 128/858, 857, 863, 846; 2/439, 452, 431, 436, 447, 426; 351/111, 112

[56] References Cited

U.S. PATENT DOCUMENTS

| | | | |
|---|---|---|---|
| 1,123,376 | 1/1915 | Rextrew | 2/431 |
| 2,395,297 | 2/1946 | Shock, Jr. | 2/447 |
| 2,534,655 | 12/1950 | Baratelli | 2/431 |
| 3,036,310 | 5/1962 | Young | 2/436 |
| 3,663,959 | 5/1972 | Loubeyre | 2/436 |
| 4,122,847 | 10/1978 | Craig . | |
| 4,240,718 | 12/1980 | Wichers | 351/62 |
| 4,391,498 | 7/1983 | Rengstorff | 351/111 |
| 4,411,263 | 10/1983 | Cook . | |
| 4,425,669 | 1/1984 | Grendol et al. | 2/436 |
| 4,502,476 | 3/1985 | Welt . | |
| 4,603,442 | 8/1986 | Barfield | 2/447 |
| 4,617,686 | 10/1986 | Nahas | 2/447 |
| 4,649,908 | 3/1987 | Ghaly . | |
| 4,688,272 | 8/1987 | Leonardi | 2/431 |
| 4,689,838 | 9/1987 | Angernam et al. | 2/436 |
| 4,741,611 | 5/1988 | Burns . | |
| 4,797,956 | 1/1989 | Boyce . | |
| 4,825,878 | 5/1989 | Kuntz et al. . | |
| 4,843,655 | 7/1989 | Hegendorfer | 2/439 |
| 4,850,058 | 7/1989 | Cheng . | |
| 4,859,048 | 8/1989 | Jannard . | |
| 4,930,885 | 6/1990 | Laschober | 2/452 |
| 4,964,714 | 10/1990 | Weymouth, Jr. | 2/436 |
| 5,056,163 | 10/1991 | Chou | 2/431 |
| 5,159,938 | 11/1992 | Laughlin . | |
| 5,243,711 | 9/1993 | Graham | 2/439 |
| 5,245,709 | 9/1993 | Shipcott | 2/436 |
| 5,261,398 | 11/1993 | Sobolik | 128/857 |
| 5,297,298 | 3/1994 | Salatka et al. | 2/447 |
| 5,302,977 | 4/1994 | Markovitz et al. | 2/426 |

FOREIGN PATENT DOCUMENTS

| | | |
|---|---|---|
| 973014 | 2/1951 | France . |
| 1148276 | 12/1957 | France . |
| 1539730 | 8/1968 | France . |
| 2301575 | 7/1973 | Germany .............. 2/447 |

Primary Examiner—Robert A. Hafer
Assistant Examiner—Michael O'Neill
Attorney, Agent, or Firm—Richard Litman

[57] ABSTRACT

A form of eye protection intended for use in protecting the eyes of a dental patient against foreign particles and contaminants basically includes a frame, a shield supported by the frame, and a strap for securing the frame in a desired position on a wearer's head. The eye protection device is structured and configured to conform to the contours of the wearer's nose and cheeks so as to form a contact seal between the eye protection device and the wearer's face. The eye protection device is further structured and configured to be angularly positionable relative to the wearer's face so as to remain spaced from the wearer's forehead and thus, preclude foreign particles and contaminants from entering the wearer's eyes.

10 Claims, 3 Drawing Sheets

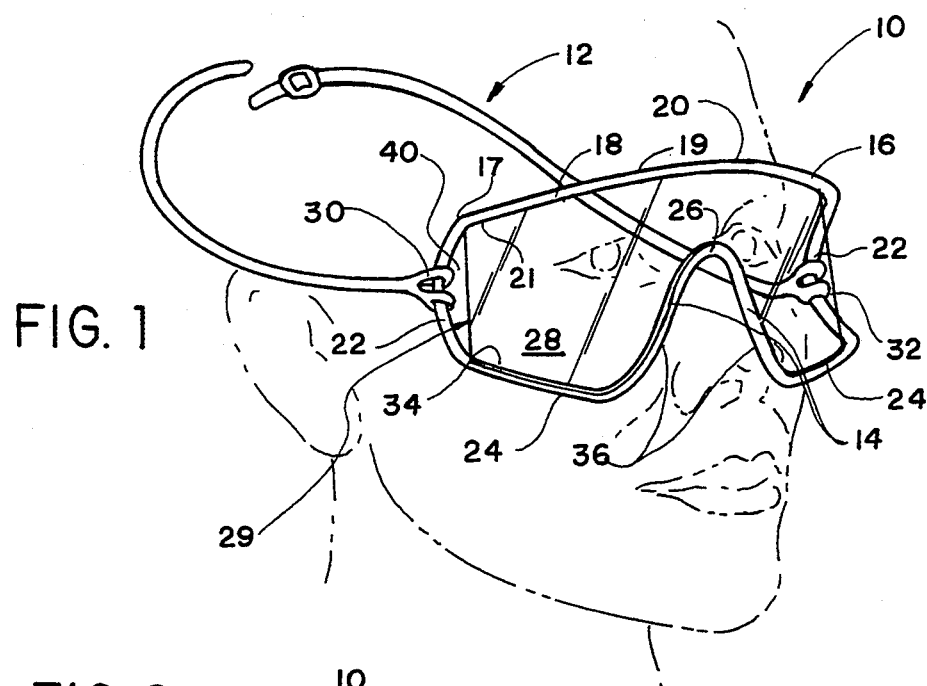
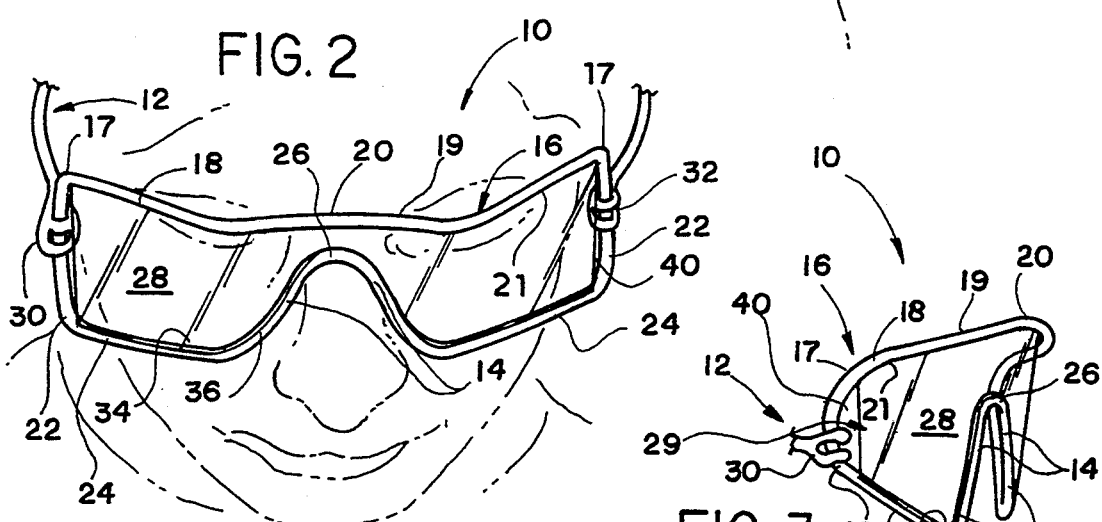
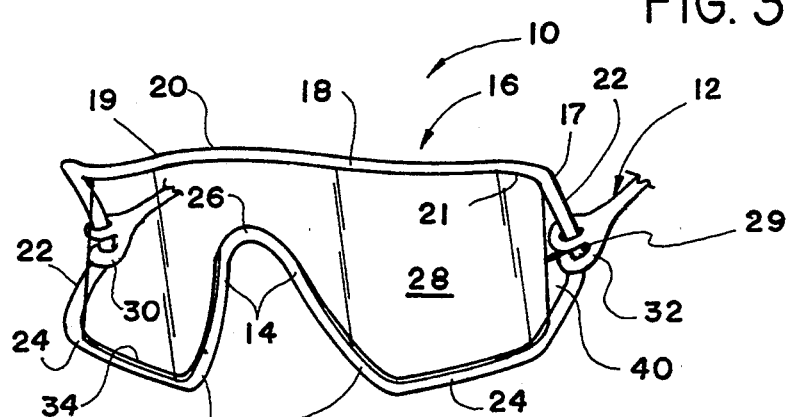

PROTECTIVE EYE SHIELD FOR DENTAL PATIENTS

BACKGROUND OF THE INVENTION

1. Field of the Invention

The present invention relates to an eye protection device and, more particularly, an eye protection device for use by a reclined dental patient during dental treatment.

2. Description of the Prior Art

Solid fragments of metal or plastic restorations, such as fillings, are commonly ejected from the patient's mouth as the patient is being treated. Contaminated fluids are likewise splattered about during many procedures. These fluids often contain pathogenic (disease causing) bacteria, viruses, and fungi that can infect the eyes of both the patient and the dental treatment facility employees.

For the protection of employees, the Occupational Safety and Health Administration (OSHA) now requires the employees to wear safety glasses with side shields while engaged in the treatment of dental patients. In addition to protecting the employees, some government regulated clinics even require safety glasses to be worn by the dental patients being treated. The patients are not only subject to risk of eye injury due to fragments and contaminants during clinical procedures, but are subject to injury by heavy and/or sharp dental instruments which are frequently handled in the proximity of the patient's eyes. If the instruments should be mishandled and dropped, serious eye injury could result. With this in mind, many private dental practitioners voluntarily provide safety glasses for use by their patients. There is a need to provide comfortable eye protection for use in protecting a dental patient against the risk of eye injury.

Eye safety has been an important concern, and eye safety protection devices have been the subject of patent protection. Typical eye protection generally contacts the wearer's face in an encirculating manner about the wearer's eyes and are purposed to protect the eye area against flying particulate matter. One such form of eye protection is shown, for example, in U.S. Pat. No. 4,850,058, issued to Chensan Cheng on Jul. 25, 1989. Cheng discloses a pair of goggles having a frontal eye shield and a cord. The shield includes a continuous rearward surface which is to accommodate the general contour of person's face. A concave recess is formed in a lower center portion of the shield for abutting the wearer's nose. An upper portion of the shield abuts snugly against the wearer's forehead. The cord is fastened to the sides of the shield to allow attachment of the shield to the wearer's face.

Another form of eye protection is shown in U.S. Pat. No. 4,122,847, issued to Robert G. Craig on Oct. 31, 1978. Craig discusses a protective eye shield specifically configured for use by surgical patients. This invention generally describes a face mask member formed of two substantially identical opposite portions joined together by a bridge portion. The mask member is designed to be secured to the user's face, substantially entirely around the user's eyes. An eye protection device similar to that shown and described by Craig above are disclosed in U.S. Pat. Nos. 4,411,263, issued to Gayle Cook on Oct. 25, 1983, 4,502,476, issued to Claire D. Welt on Mar. 5, 1985, and 4,649,908, issued to Maurice S. Ghaly on Mar. 17, 1987.

Yet another form of eye protection is disclosed in U.S. Pat. No. 4,797,956, issued to Elvin L. Boyce on Jan. 17, 1989. Boyce describes a protective face mask including a flexible transparent material which is generally flat in shape. A moldable stiffener is attached to a bottom edge of the transparent material and permits the transparent material to be molded to conform to the wearer's nose and cheeks. Means for spacing the transparent material away from the wearer's eyes is attached to an upper edge of the transparent material opposite the moldable stiffener. A single elastic band is attached to two sides of the transparent material for drawing the eye shield closely to the user's face.

Alternative eye protection is disclosed in U.S. Pat. No. 5,159,938, issued to Patrick E. Laughlin on Nov. 3, 1992. Laughlin describes an eye shield that indexes to an inhalation gas providing nose hood and the hood's hoses to provide secure eye protection to a dental patient during the performance of dental procedures. The shield further indexes to the patient's temples and forehead to provide secure and comfortable positioning of the same. The shield cooperates with the inhalation hood to shield against materials reaching the patient's eyes.

Other possible forms of eye protection, including shields, eyeglasses, lenses, and the like, are disclosed in U.S. Pat. Nos. 4,825,878, issued to David H. Kuntz et al. on May 2, 1989, 4,741,611, issued to Dennis L. Burns on May 3, 1988, and 4,859,048, issued to James H. Jannard on Aug. 22, 1989. Not one of these patents discloses a protective shield configured to conform to a wearer's face.

Other patents which may be deemed of interest include French Pats Nos. 1,539,730, issued to M. Francisque Ginet and published on August 1968, 1,148,276, issued to Marie-Louise Mauries and published on Dec. 5, 1957, and 973,014, issued to Nelly-Claire-Eugenie Dermont Maradji and published on Feb. 6, 1951. These French Patents follow the general characteristics of the above cited U.S. Patents.

According to the present invention, a comfortable form of eye protection is provided for reducing the risk of injury to a dental patient's eyes. None of the above inventions and patents, taken either singly or in combination, is seen to describe the instant invention as claimed.

SUMMARY OF THE INVENTION

The present invention is related to eye safety protection for use in a dental treatment environment and, more particularly, to eye safety protection for use by dental patients, either awake or anesthetized, in a reclined position. The eye safety protection basically includes a frame, a shield supported by the frame, and a retention strap for retaining the frame, and the shield supported thereby, on the wearer.

The geometry of the frame ensures that particulate matter is deflected by the shield away from the wearer's eyes. The frame includes a superior rim and oppositely disposed lateral rims, bottom rims, and inferior rims integrally joined so as to form a frame of unitary construction.

The inferior rims maintain uninterrupted contact with the lateral aspects of the wearer's nose and/or with the wearer's cheeks in the areas immediately adjacent to the wearer's nose. Facial contact by the bottom rims continues laterally to where the curvature of the wearer's cheek is in distinct transition between the front and side aspects of the wearer's face. Beyond this point of the wearer's face, eye protection by maintenance of a physical seal is typically not necessary.

The inferior rims converge at an inferior apex to form an inferior rim complex which is basically parabolic in shape. The inferior rims diverge downwardly from the inferior apex at an average angle of 45°. Upon placing the frame on the wearer's face, the frame is adjustable, or positionable, upward or downward until the naturally parabolic outer contours of the wearer's nose are juxtaposed to the inferior rims of the frame, thus forming a contact seal. The proper position for the inferior apex is not necessarily in the same relative superior/inferior position along the length of each and every wearer's nose.

With the frame positioned properly on the wearer's face, the superior rim extends in a superior direction sufficiently to provide protection to the areas including and immediately superior to the wearer's eyebrows. The resting horizontal distance from the superior rim to the wearer's forehead is a variable result of the final position and orientation of the shield, as determined by the placement related factors discussed above. The location of the superior rim is in front of a vertical plane define by that plane within which the inferior rims lie. This arrangement allows space for rearward rotation of the frame, as would occur if the wearer has a less prominent nose or more prominent cheeks. In any case, the superior rim must be sufficiently forward to avoid contact with the wearer's face. If the frame contacts the wearer's face anywhere above the level of the inferior apex, the desired contact by either the inferior rims or the inferior apex may be obstructed.

The mode of strap attachment must allow pivotal movement of the frame in order to achieve a desired contact of the inferior rims and/or inferior apex. In one embodiment, the strap may be provided with a single loop at each end thereof. These loops may slide over respective hooks which are integral with respective lateral rims. In this embodiment, the strap connects with the lateral rims at a vertical level generally even with the middle of the inferior rims. It is this position of the strap relative to the bottom rims and the inferior apex that results in consistent contact of the inferior apex with some point along the crest of the wearer's nose.

In an alternative embodiment, the strap slidably engages the lateral rims of the frame. The angles formed between the lateral rims and the superior rim, and the angles formed between the lateral rims and the bottom rims, are obtuse. If the upper and lower segments of the lateral rims meet to form a very acute angle, a moveable strap would tend to slide toward this angle, particularly if the strap is loosely attached. For this reason a gentle curve of the lateral rims is preferable. Curved lateral rims may enable tension vectors placed on the frame by the strap to be more generally perpendicular to the segment of the frame where the strap is positioned. This is demonstrated where facial anatomy necessitates exaggerated forward or backward tilting of the shield. Movement of the strap beyond an acceptable range can be physically obstructed by the lateral edges of the transparent shield that is contained within the frame.

In either embodiment, the strap is preferably made of an elastic material and is preferably adjustable lengthwise to allow for significant variations in the sizes of the wearer's head beyond the that of elastic range of the strap. In the event that the shield is made of a material intended to withstand heat or chemical sterilization, any part of the strap that is not capable of withstanding sterilization treatment must be detachable from such a shield.

Accordingly, it is a principal object of the present invention to provide a comfortable form of eye protection for use by dental patients and which may universally conform to the facial contours of various wearers.

It is another object that the eye protection be structured and configured to conform to the contours of the patient's nose and cheeks so as to form a contact seal therebetween, virtually eliminating the need for a physical sealing element, while remaining in a spaced relationship to the wearer's forehead.

It is another object that the eye protection prevent particulate matter from entering into a dental patient's eyes while the dental patient is in a reclined position.

It is a further object that the eye protection includes a frame which, when properly positioned, is structured and configured to rest only on the patient's nose and cheeks and not against the patient's forehead.

Still another object is that the eye protection be provided with retention straps, preferably elastic retention straps, positionally adjustable to allow the frame thereof to be positioned to rest in a desired orientation upon the patient's cheeks and nose.

It is another object that the strap be adjustable lengthwise to accommodate different size heads of various users and to vary the pressure of the frame resting against the wearer's face.

It is another object that the eye protection be fabricated of light weight materials to improve the comfort of the same.

It is an object to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is an environmental front perspective view of an eye protection device according to the present invention.

FIG. 2 is an environmental top perspective of the eye protection device shown in FIG. 1.

FIG. 3 is a side perspective view of the eye protection device.

FIG. 4 is a front perspective view of the eye protection device.

Similar reference characters denote corresponding features consistently throughout the attached drawings.

DETAILED DESCRIPTION OF THE PREFERRED EMBODIMENTS

Figure 7:
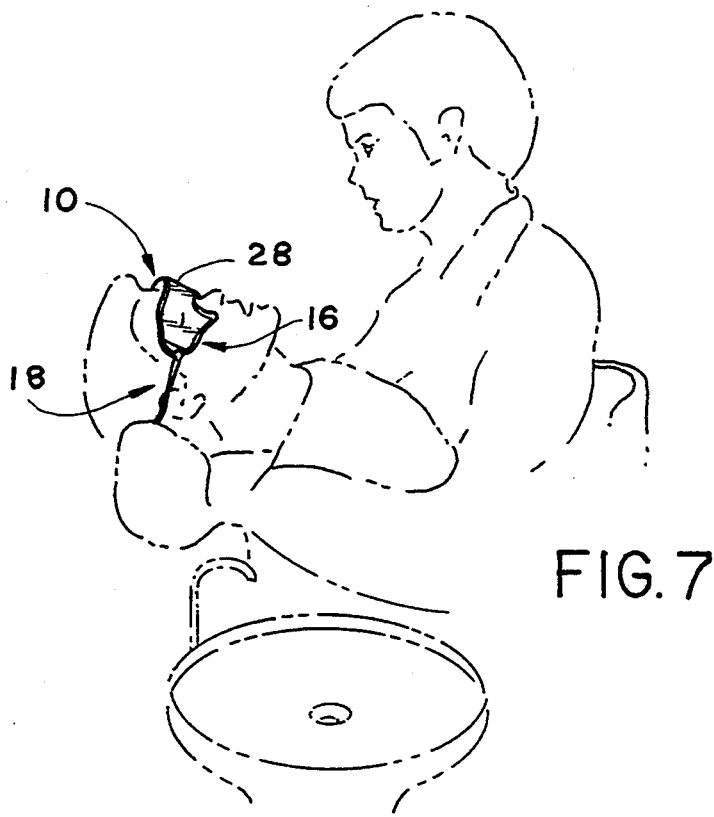
FIG. 7 is an environmental side elevational view of the eye protection device, as shown in FIG. 1, worn by reclining dental patient.

The present invention, as shown in FIGS. 1 through 3, is an eye safety protection device 10 for use by dental patients. The eye protection device 10 is intended for use by a dental patient in a reclined position and is intended to protect the dental patient from fragments and contaminants originating from the patient's oral region during dental treatment, as is shown in FIG. 7. The eye protection device 10 includes a frame 16, a shield 28 supported by the frame 16, and a retention strap 12 for holding the frame 16 and, in turn, the shield 28 upon the wearer's face.

Now, referring to FIGS. 1 through 5, the geometry of the frame 16 ensures that particulate matter is deflected by the shield 28 away from the wearer's eyes. The frame 16 includes a superior rim 18 and oppositely disposed lateral rims 22, bottom rims 24, and inferior rims 14 integrally joined together form so as to form a frame be of unitary construction.

The superior rim 18 is generally horizontal and extends bilaterally from the superior apex 20 in a slightly rearward angle as from the superior apex 20. The superior rim 28 continues rearwardly and in a downwardly bent angle toward the lateral rims 22 and are contiguous with the lateral rims 22. The lateral rims 22 are, in turn, contiguous with respective bottom rims 24 which are, in turn, contiguous with respective inferior rims 14.

The inferior rims 14 lie in a vertical plane, extending superiorly and passing behind a superior apex 20, located at the center of the superior rim 18, and the medial majority 19 of the superior rim be. As the superior rim 18 is directed more posteriorly at its lateral extents 21, the lateral ends 17 of the superior rim 18 are located posteriorly of a plane defined by the inferior rims 14. The inferior rims 14 maintain uninterrupted contact with the lateral aspects of the wearer's nose and/or with the wearer's cheeks in the areas immediately adjacent to the wearer's nose. Facial contact by the bottom rims 24 continues laterally to where the curvature of the wearer's cheek is in distinct transition between the front and side aspects of the wearer's face. Beyond this point of the wearer's face, eye protection by maintenance of a physical seal is typically not necessary.

It should be noted that continuous facial contact is made with the contoured cheek rest areas 36 of the frame 16, that is to say, the single and curved linear areas of the frame 16 comprised of the inferior apex 26, the inferior rims 14, and the bottom rims 24, as opposed to facial contact being made with discrete areas of the frame 16.

The inferior rims 14 converge at an inferior apex 26, adjoining the oppositely disposed inferior rims 14, to form an inferior rim complex which is basically parabolic in shape. The inferior rims 14 diverge downwardly from the inferior apex 26 at an average angle of 45°. Upon placing the frame 16 on the wearer's face, the frame 16 is adjustable, or positionable, upward or downward until the naturally parabolic outer contours of the wearer's nose are juxtaposed to the inferior rims 14 of the frame 16, thus forming a contact seal. The proper position for the inferior apex 26 is not necessarily in the same relative superior/inferior position along the length of each and every wearer's nose. After having formed a contact seal between the inferior rims 14 and the wearer's nose and/or cheeks, the frames 16 forward rotational orientation has likely varied about an imaginary axis that is parallel to, but not necessary coincident with, an imaginary line that passes through the points where the strap 12 connects to each lateral rim 22.

With the frame 16 positioned properly on the wearer face, the superior rim 18 extends in a superior direction sufficiently to provide protection to the areas including and immediately superior to the wearer's eyebrows. The resting horizontal distance from the superior rim 18 to the wearer's forehead is a variable result of the final position and orientation of the shield 28, as determine, by the placement related factors discussed above. The location of the superior rim 18 is in front of a vertical plane within which the inferior rims 14 lie. This arrangement allows space for rearward rotation of the shield 28, as would occur if the wearer has a less prominent nose or more prominent cheeks. In any case, the superior rim 18 must be sufficiently forward to avoid contact with the wearer's face. If the shield 28 contacts the wearer's face anywhere above the level of the inferior apex 26, the desired contact by either the inferior rims 14 or the inferior apex 26 may be obstructed.

Figure 5:
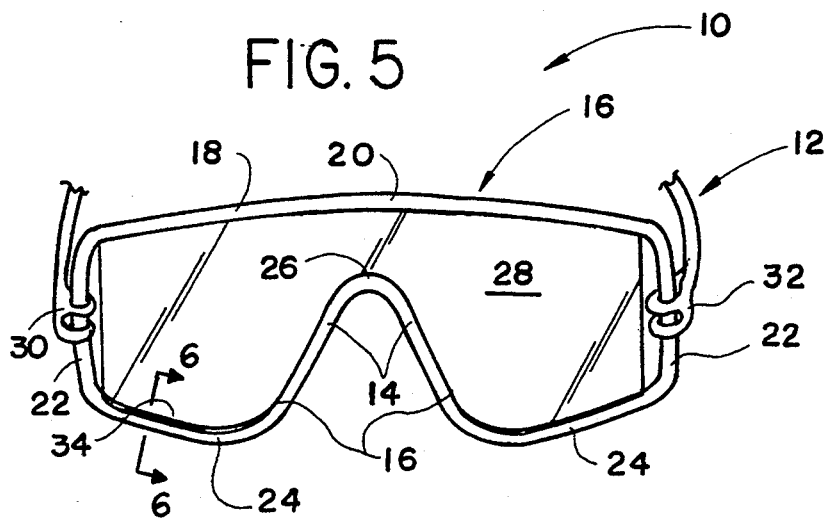
FIG. 5 is a front elevational view of the eye protection device.
Figure 6:
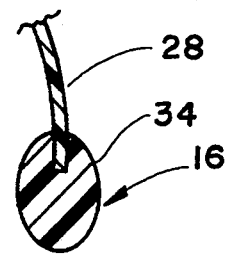
FIG. 6 is a cross-sectional view of the frame and shield drawn along lines 6—6 of FIG. 5.

The frame 16 has an inner groove 34, as shown in FIG. 6, that accommodates the shield 28. The shield 28 fits within an inner area bounded by the frame 16. In one embodiment, the shield 28 extends from the superior rim 18 to the bottom rims 24 and the inferior rims 14, yielding a ¼ inch gap or opening 40 between the shield 28 and the lateral rims 22.

The mode of strap 12 attachment must allow pivotal movement of the frame 16 in order to achieve a desired contact of the inferior rims 14 and/or inferior apex 26. In one embodiment, the strap 12 attaches to the eye protection device 10 in the area of opening 40. The opening 40 is formed between the lateral rims 22 and the lateral edge 29 of the shield 28. The strap ends 30, 32 are free to slide along the later rims 22. The angles formed between the lateral rims 22 and the superior rim 18, and the angles formed between the lateral rims 22 and the bottom rims 24, are obtuse. If the upper and lower segments of the lateral rims 22 meet to form a very acute angle, a moveable strap 12 would tend to slide toward this angle, particularly if the strap 12 is loosely attached. For this reason a gentle curve of the lateral rims 22 is preferable. Curved lateral rims 22 may enable tension vectors placed on the frame 16 by the strap 12 to be more generally perpendicular to the segment of the frame 16 where the strap 12 is positioned. This is demonstrated where facial anatomy necessitates exaggerated forward or backward tilting of the shield 28. Movement of the strap 12 beyond an acceptable range can be physically obstructed by the lateral edges of the transparent shield 28 that is contained within the frame 16.

Figure 8:
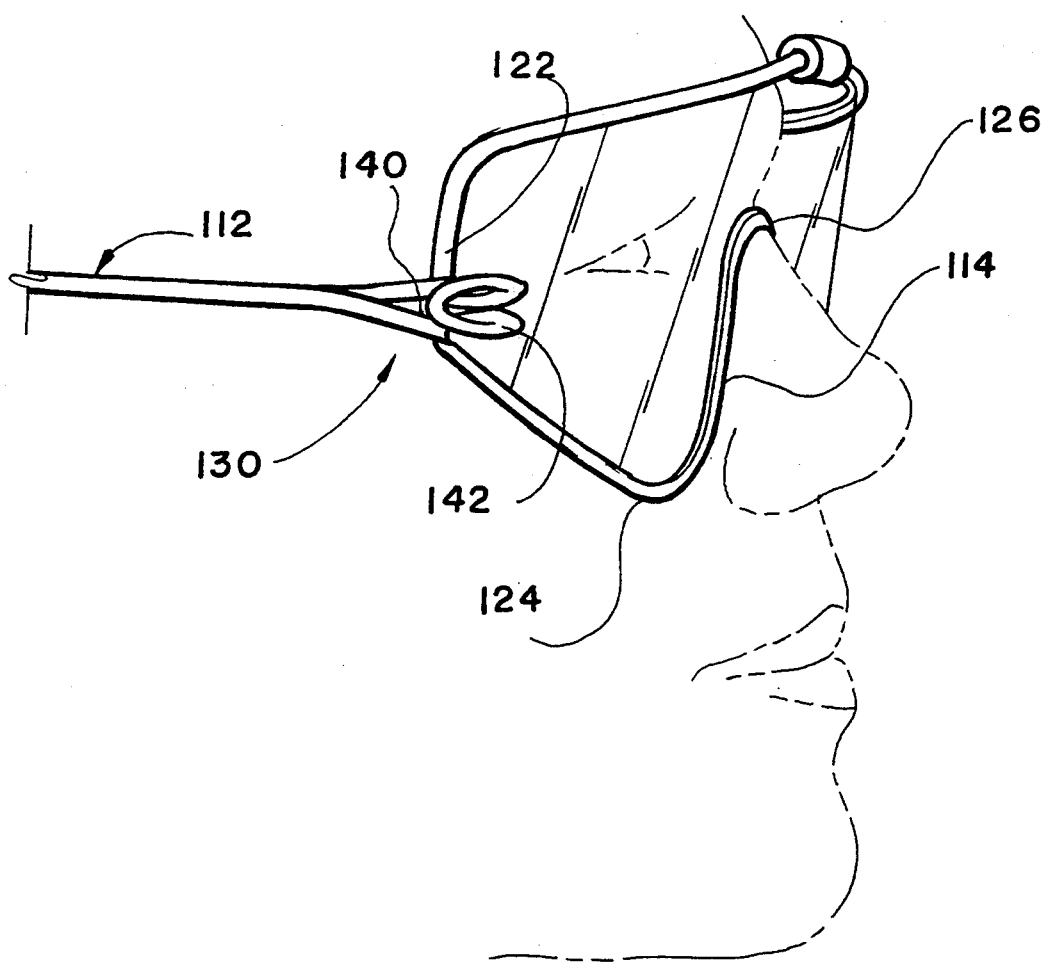
FIG. 8 is an environmental side elevational view of an alternative form of protection.

In an alternative embodiment, shown in FIG. 8, the strap 112 may be provided with a single loop 140 at each end 130 thereof. These loops 140 may slide over respective hooks 142 which are integral with respective lateral rims 122. Portions of the lateral rims 122 are configured to form the integral hooks 142. In this embodiment, the strap 112 connects with the lateral rims 122 at a vertical level generally even with the middle of the inferior rims 114. It is this position of the strap 112 relative to the bottom rims 124 and the inferior apex 126 that results in consistent contact of the inferior apex 126 with some point along the crest of the wearer's nose.

In either embodiment, the strap 12, 112 transfers tensile force on the frame 16 when the eye protection device 10 is properly adjusted on the wearer. A lengthwise adjustability of the strap 12, 112 enables the pressure of the frame 16 against the wearer's face to be adjusted.

The strap 12, 112 is preferably made of an elastic material and is preferably adjustable lengthwise to allow for significant variations in the sizes of the wearer's head beyond the elastic range of the strap 12, 112. In the event that the shield 28 is made of a material intended to withstand heat or chemical sterilization, any part of the strap 12,112 that is not capable of withstanding sterilization treatment must be detachable from such a shield 28.

It is to be understood that the present invention is not limited to the embodiments described above, but encompasses any an all embodiments within the scope of the following claims.

I claim:

1. An eye protection device, comprising: a frame having a rim including:
    a superior rim (18) having a superior apex (20), a medial majority (19), lateral extents (21), and lateral ends (17), said lateral extents (21) extending bilaterally from said medial majority (19) and terminating at said lateral ends (17),
    oppositely disposed lateral rims (22) contiguous with said lateral ends (17) of said superior rim (18),
    oppositely disposed bottom rims (24) contiguous with respective ones of said lateral rims (22), and
    a inferior rim complex contiguous with and adjoining said oppositely disposed bottom rims, said inferior rim complex including oppositely disposed inferior rims (14) and an inferior apex (26) adjoining said inferior rims (14), said inferior rim complex being generally parabolic in shape and diverging downwardly from said inferior apex at a predetermined angle, said inferior rims (14) being located in a plane passing behind said superior apex (20) and said medial majority (19) of said superior rim (18), and said inferior rims (14) being anterior to said lateral ends (17) of said superior rim (18);
    a shield (28) supported by said frame, said shield having lateral edges (29), said lateral edges being spaced from said lateral rims (22), and said lateral edges defining an opening (40) in cooperation with said lateral rims; and
    a strap (12) for retaining said frame on a wearer, said strap having means for attaching said strap to said lateral rims, said strap being attached to said lateral rims, and said means for attaching said strap to said lateral rims being free to slide along said lateral rims defining said opening in cooperation with said lateral edges of said shield.

2. An eye protection device according to claim 1, wherein said shield is substantially transparent.

3. An eye protection device according to claim 1, wherein said means for attaching is structured and configured to enable said strap to be releasably attached to said lateral rims.

4. An eye protection device according to claim 1, wherein said strap includes means for selectively adjusting said strap to one of a plurality of lengths.

5. An eye protection device according to claim 1, wherein said strap is fabricated of an elastomeric material.

6. An eye protection device, comprising:
    a frame having a rim including:
    a superior rim having a superior apex (20), a medial majority (19), lateral extents (21), and lateral ends (17), said lateral extents (21) extending bilaterally from said medial majority (19) and terminating at said lateral ends (17),
    oppositely disposed lateral rims (122) contiguous with said lateral ends (17) of said superior rim, wherein portions of said lateral rims (122) are shaped to form hooks (142),
    oppositely disposed bottom rims (124) contiguous with respective ones of said lateral rims (122), and
    a inferior rim complex contiguous with and adjoining said oppositely disposed bottom rims (124), said inferior rim complex including oppositely disposed inferior rims (114) and an inferior apex (126) adjoining said inferior rims, said inferior rim complex being generally parabolic in shape and diverging downwardly from said inferior apex at a predetermined angle, said inferior rims being located in a plane passing behind said superior apex (20) and said medial majority (19) of said superior rim, and said inferior rims (114) being anterior to said lateral ends (17) of said superior rim;
    a shield 128) supported by said frame; and
    a strap (112) for retaining said frame on a wearer, said strap having means for attaching (140) said strap to said hooks (142), and said strap being attached to said hooks.

7. An eye protection device according to claim 6, wherein said shield is substantially transparent.

8. An eye protection device according to claim 6, wherein said means for attaching is structured and configured to enable said strap to be releasably attached to said hooks.

9. An eye protection device according to claim 6, wherein said strap includes means for selectively adjusting said strap to one of a plurality of lengths.

10. An eye protection device according to claim 6, wherein said strap is fabricated of an elastomeric material.

* * * * *